United States Patent
Fujimori et al.

(10) Patent No.: US 9,957,245 B2
(45) Date of Patent: May 1, 2018

(54) CATALYST FOR SYNTHESIZING THEAFLAVINS AND METHOD FOR SYNTHESIZING THEAFLAVINS

(71) Applicant: NBC MESHTEC INC., Tokyo (JP)

(72) Inventors: Yoshie Fujimori, Tokyo (JP); Tsuruo Nakayama, Tokyo (JP); Tomokazu Nagao, Tokyo (JP)

(73) Assignee: NBC MESHTEC INC., Tokyo (JP)

(*) Notice: Subject to any disclaimer, the term of this patent is extended or adjusted under 35 U.S.C. 154(b) by 0 days. days.

(21) Appl. No.: 15/320,347

(22) PCT Filed: Jun. 29, 2015

(86) PCT No.: PCT/JP2015/003253
§ 371 (c)(1),
(2) Date: Dec. 20, 2016

(87) PCT Pub. No.: WO2015/198614
PCT Pub. Date: Dec. 30, 2015

(65) Prior Publication Data
US 2017/0158660 A1  Jun. 8, 2017

(30) Foreign Application Priority Data
Jun. 27, 2014 (JP) .................... 2014-133027

(51) Int. Cl.
*C07D 311/00* (2006.01)
*C07D 311/22* (2006.01)
(Continued)

(52) U.S. Cl.
CPC ............. *C07D 311/22* (2013.01); *B01J 23/42* (2013.01); *B01J 23/44* (2013.01); *B01J 23/52* (2013.01);
(Continued)

(58) Field of Classification Search
CPC ... C07D 311/22; B01J 35/023; B01J 35/0013; B01J 23/42; B01J 23/89; B01J 23/52; B01J 23/44; C07B 61/00
(Continued)

(56) References Cited

U.S. PATENT DOCUMENTS

2004/0097430 A1  5/2004 Zhao et al.
2004/0097432 A1  5/2004 Roh-Schmidt et al.
(Continued)

FOREIGN PATENT DOCUMENTS

CN  101990463  *  3/2011
JP  46-2265  10/1971
(Continued)

OTHER PUBLICATIONS

International Preliminary Report on Patentability dated Dec. 27, 2016 in corresponding International Application No. PCT/JP2015/003253.
(Continued)

*Primary Examiner* — Taylor V Oh
(74) *Attorney, Agent, or Firm* — Wenderoth, Lind & Ponack, L.L.P.

(57) ABSTRACT

The objective/problem addressed by the present invention is to provide a novel technique pertaining to theaflavins synthesis. The present invention pertains to: a theaflavins synthesis catalyst characterized in having a base comprising an inorganic material, and metal nanoparticles anchored to the base, said particles measuring 0.5-100 nm in diameter; and a theaflavins synthesis method in which the catalyst is used.

4 Claims, 3 Drawing Sheets

(51) Int. Cl.
- *B01J 23/42* (2006.01)
- *B01J 23/44* (2006.01)
- *B01J 23/52* (2006.01)
- *B01J 23/89* (2006.01)
- *B01J 35/00* (2006.01)
- *B01J 35/02* (2006.01)
- *C07B 61/00* (2006.01)

(52) U.S. Cl.
  CPC ........... *B01J 23/89* (2013.01); *B01J 35/0013* (2013.01); *B01J 35/023* (2013.01); *C07B 61/00* (2013.01)

(58) Field of Classification Search
  USPC ........................................................ 549/399
  See application file for complete search history.

(56) References Cited

U.S. PATENT DOCUMENTS

| | | | |
|---|---|---|---|
| 2007/0098765 A1 | 5/2007 | Zhao et al. | |
| 2009/0181079 A1 | 7/2009 | Zhao et al. | |
| 2014/0308592 A1 | 10/2014 | Maki et al. | |
| 2015/0231610 A1 | 8/2015 | Sakurai et al. | |

FOREIGN PATENT DOCUMENTS

| | | |
|---|---|---|
| JP | 2004-155784 | 6/2004 |
| JP | 2004-256459 | 9/2004 |
| JP | 2005-523242 | 8/2005 |
| JP | 2010-35548 | 2/2010 |
| JP | 2010-138103 | 6/2010 |
| JP | 2011-172514 | 9/2011 |
| WO | 2009/125847 | 10/2009 |
| WO | 2013/035741 | 3/2013 |
| WO | 2014/038504 | 3/2014 |

OTHER PUBLICATIONS

International Search Report issued Sep. 15, 2015 in International Application No. PCT/JP2015/003253.
Extended European Search Report dated Jan. 2, 2018 in corresponding European Patent Application No. 15811544.4.

* cited by examiner

CATALYST FOR SYNTHESIZING THEAFLAVINS AND METHOD FOR SYNTHESIZING THEAFLAVINS

TECHNICAL FIELD

The present invention relates to a catalyst usable for synthesis of theaflavins and a method for synthesizing theaflavins.

BACKGROUND ART

Attention has been attracted to various functional substances contained in Japanese tea that has been drunk by Japanese for a long time due to current boom of health. A representative example thereof as catechins. Catechins were first confirmed by Dr. Tsujimura, et al. in 1929 at The Institute of Physical and Chemical Research. Then, various functions of catechins such as an antioxidation action, an antibiotic action, prevention of cancer, and decrease in blood cholesterol level have been found. Products such as foods for specified health uses and supplements have been made from catechins.

However, production of green tea that contains a large amount of catechins is restricted to some regions such as Japan and China, and fermented tea such as black tea and oolong tea is produced in about 80% of the world. In recent years, it has been clear that the fermented tea contains substances having the same function as that of catechins, which are called theaflavins, and attention has been attracted (Patent Literature 1). Further, a method for synthesizing theaflavins has been studied (Patent Literatures 2 and 3).

CITATION LIST

Patent Literature

Patent Literature 1: JP2004-155784
Patent Literature 2: JP2010-35548
Patent Literature 3: JP2011-172514

SUMMARY OF INVENTION

Technical Problem

However, a method using an enzymatic reaction or a cultured cell, as described in Patent Literatures 2 and 3, has problems such as very severe conditions for synthesis, low handling ability, and difficult removal of an enzyme after the reaction.

It is an object of the present invention to provide a novel technique pertaining to theaflavins synthesis.

Solution to Problem

Specifically, the gist of the present invention is as follows:

[1] A catalyst for synthesizing theaflavins having a base having an anchored part including an inorganic material on a surface, and metal nanoparticles that are anchored to the anchored part and have a particle diameter of 0.5 nm or more and 100 nm or less.

[2] The catalyst for synthesizing theaflavins according to [1], wherein the metal nanoparticles are one or two or more selected from the group consisting of Au, Pd, Pt, and oxides thereof.

[3] The catalyst for synthesizing theaflavins according to [1] or [2], wherein the anchored part includes a metal oxide.

[4] The catalyst for synthesizing theaflavins according to [3], wherein the metal oxide is one or two or more compounds selected from the group consisting of $SiO_2$, $ZrO_2$, $Fe_2O_3$, and $TiO_2$.

[5] A method for synthesizing theaflavins including bringing the catalyst for synthesizing theaflavins according to any one of [1] to [4] into contact with a catechin aqueous solution that is an aqueous solution in which pyrogallol-type catechin and catechol-type catechin are dissolved, to synthesize theaflavins.

Advantageous Effects of Invention

The present invention can provide a novel technique pertaining to theaflavins synthesis.

DESCRIPTION OF EMBODIMENTS

Hereinafter, an embodiment of the present invention will be described in detail with reference to the drawings.

A catalyst for synthesizing theaflavins of this embodiment has a base having an anchored part including an inorganic material on a surface, and metal nanoparticles that are anchored to the anchored part and have a particle diameter of 0.5 nm or more and 100 nm or less. When the metal nanoparticles are anchored to the anchored part including an inorganic material on the surface of the base, the composite has very high oxidation catalytic ability. The metal nanoparticles can be anchored to the anchored part by various methods described below. When the metal nanoparticles are converted into particles using a reductant or the like without the base, the metal particles may be aggregated. For this reason, loss of activity is considered. In this embodiment, the metal nanoparticles are anchored to the anchored part on the surface of the base including an inorganic material. Therefore, the aggregation of the metal nanoparticles can be prevented.

The base of this embodiment is not particularly limited as long as the base has the anchored part including an inorganic material. Specific examples of the base having the anchored part may include a base of which surface is constituted by an inorganic material, and a base of which the whole is constituted by an inorganic material.

The anchored part may be constituted by one or two or more of zeolite, apatite, a carbon material such as activated carbon, diatomaceous earth, and a metal oxide. Among these, it is preferable that the anchored part be a metal oxide.

A method of forming the anchored part from the metal oxide is not particularly limited. Examples thereof may include a method of electrochemically forming a thin coating film of the metal oxide by anodic oxidation, a method of oxidizing a metal surface by a thermal treatment, and a method of forming an oxidized thin film by sputtering or an ion plating method. The whole base may be constituted by the metal oxide.

Since the anchored part is constituted by the metal oxide, exchange of oxygen molecules is active. Therefore, the catalytic activity can be enhanced more. Examples of the metal oxide may include oxides of silicon, zirconium, zinc, titanium, chromium, iron, cooper, tin, and aluminum. For example, the anchored part may be constituted by one or two or more of these metal oxides. It is particularly preferable that the anchored part be constituted by one or two or more of $SiO_2$, $ZrO_2$, $Fe_2O_3$, and $TiO_2$ since the catalytic activity is further enhanced due to a relation with the amount of the metal nanoparticles anchored.

For example, the metal nanoparticles according to this embodiment may be one or two or more selected from the group consisting of gold (Au), metal palladium (Pd), platinum (Pt), and oxides thereof. Specifically, one or two or more selected from the group consisting of gold, metal palladium, platinum, a gold oxide, a palladium oxide, and a platinum oxide may foe used as the metal nanoparticles according to this embodiment.

Metal palladium refers to palladium having a valence of 0. Metal palladium may be usually obtained by reducing divalent and/or tetravalent palladium ions using a reductant (e.g., hydrazine, formaldehyde, tartaric acid, citric acid, glucose, tin chloride, sodium borohydride, sodium phosphite, and sodium hypophosphite). In this case, all of palladium may not be in a metal state.

The metal nanoparticles herein refer to metal particles having a particle diameter of less than 1 μm.

In this embodiment, the average particle diameter of the metal nanoparticles is preferably 0.5 nm or more and 100 nm or less, more preferably 0.5 nm or more and 20 nm or less, and further preferably 0.5 nm or more and 10 nm or less. A substance having an average particle diameter of less than 0.5 nm is likely to be more unstable than a substance having an average particle diameter of 0.5 nm or more, and a substance having an average particle diameter of more than 100 nm has a catalytic activity lower than a substance having an average particle diameter of 100 nm or less. On the other hand, when the average particle diameter is 100 nm or less (more preferably 20 nm or less, and further preferably 10 nm or less), the catalytic activity is further enhanced.

The average particle diameter herein refers to an average of 300 or more particle diameters of the metal nanoparticles that are actually measured in a TEM image.

The particle diameter may be adjusted, for example, by adjustment of pH of a solution during preparation by a publicly known method.

A method of anchoring the metal nanoparticles to the anchored part is not particularly limited, and may be appropriately set. For example, the metal nanoparticles may be anchored to the anchored part on the surface of the base by a binder, heating and drying, or the like.

The metal nanoparticles may be anchored by applying colloid to a part on the surface of the base that becomes the anchored part, followed by drying.

When metal palladium or a palladium oxide is anchored to the base, palladium ions may be anchored by absorption through a chemical method such as a zeta potential between the palladium ions and the base and diffusion of the palladium ions. Alternatively, the base is immersed in an aqueous solution containing palladium ions to be coated therewith, and then immersed in an aqueous solution containing a reductant such as an organic acid, formaldehyde, and hydrazine, or reduced in a hydrogen reduction atmosphere. Thus, nanoparticles of the metal palladium or palladium oxide may be anchored to the anchored part.

For example, the metal nanoparticles may have a hemispheric shape or the like and be closely jointed to the anchored part. Thus, a junction interface peripheral part may be formed at the anchored part by the junction. At that time, the metal nanoparticles are directly jointed to the anchored part using a difference in zeta potential between the inorganic material constituting the anchored part and the metal nanoparticles. The junction herein represents that the anchored part and the metal nanoparticles are brought into contact with each other at a surface (junction interface), resulting in anchoring. The junction interface peripheral part herein refers to a peripheral part (perimeter) of the junction interface. Herein, directly jointed represents that the anchored part on the surface of the base and the metal nanoparticles are anchored without another material, such as a binder, interposed therebetween.

The metal nanoparticles are directly jointed to the anchored part of the surface of the base, and the junction interface peripheral part is exposed to a surface of the catalyst. When the catalyst having the junction interface peripheral part between the base and the metal nanoparticles acts on catechol-type catechin and pyrogallol-type catechin, a synthesis reaction of theaflavins further proceeds. This will be specifically described. It is estimated that oxygen defects tend to occur at the junction interface peripheral part and activation of oxygen molecules and hydrogen molecules proceeds at the part. Therefore, the presence of the junction interface peripheral part is advantageous for increase in oxidation catalytic activity and selectivity. Accordingly, in this embodiment, if is preferable that the catalyst have a junction interface peripheral part formed by junction between the metal nanoparticles and the anchored part.

A method of anchoring the metal nanoparticles in a state where the junction interface peripheral part is formed by direct jointing to the surface of the base is not particularly limited. Specific examples of the method may include methods such as coprecipitation, deposition-precipitation, a sol-gel method, precipitation by dropping neutralization, addition of a reductant, precipitation by pH-control neutralization, and addition of carboxylic acid metal salt. The methods can be appropriately used depending on the kind of the inorganic material constituting the base.

Hereinafter, a method of preparing the catalyst for synthesizing theaflavins of this embodiment using a gold compound and based on deposition-preparation as an example of method of anchoring the metal nanoparticles will be specifically described. In a specific method of the deposition-precipitation, an aqueous solution in which the gold compound is dissolved is first heated to 20 to 90° C., and preferably 50 to 70° C., and the pH of the solution is adjusted to 3 to 10, and preferably 5 to 8 with an alkaline solution with stirring. After that, the inorganic material to become the base is added to the aqueous solution, and the mixture is dried by heating at 100 to 200° C., to obtain the catalyst for synthesizing theaflavins of this embodiment.

Examples of the gold compound that can be used in preparation of the gold compound aqueous solution may include $HAuCl_4.4H_2O$, $NH_4AuCl_4$, $KAuCl_4.nH_2O$, $KAu(CN)_4$, $Na_2AuCl_4$, $KAuBr_4.2H_2O$, and $NaAuBr_4$. The concentration of the gold compound in the gold compound aqueous solution is not particularly limited, and is preferably $1\times10^{-2}$ to $1\times10^{-5}$ mol/L.

The amount of the metal nanoparticles to be supported on the base is not particularly limited, and is preferably 0.5 to 20% by mass, and more preferably 0.5 to 10% by mass, relative to the amount of the base. When the metal nanoparticles are supported at a rate of higher than 20% by mass, the metal nanoparticles are likely to be aggregated and a reduction-oxidation action is decreased as compared with a case where the amount falls within the range.

In the catalyst for synthesizing theaflavins of this embodiment, the metal nanoparticles may be anchored to the surface of the base including the inorganic-material and oxide particles of titanium, aluminum, iron, and the like may be further supported on the surface. A method of supporting oxide particles on the surface of the base is not particularly limited. For example, the oxide particles may be supported on the base by a thermal spraying method. The oxide particles supported on the base can suppress attachment of a substance that inhibits catalytic activity to the metal nanoparticles. Therefore, the reduction-oxidation action can be stably maintained over an extended period of time.

The catalyst for synthesizing theaflavins of this embodiment can have various forms. A method of adjusting the form is not particularly limited. Fox example, the form of the catalyst can be molded into any form by adjusting a form of the base. The catalyst for synthesizing theaflavins of this embodiment can have a form such as a powder form, a granular form, and a tablet form obtained by molding under pressure. When as the base, a woven fabric, non-woven fabric, or sheet formed of fibrous inorganic materials or a foil-shaped or plate-shaped metal oxide is used, the catalyst for synthesizing theaflavins of this embodiment can have various forms such as a filter shape and a sheet shape.

When the catalyst for synthesizing theaflavins of this embodiment has a form such as a powder form, a granular forts, and a tablet form obtained by molding under pressure, the catalyst can be contained in a fibrous structure or is fixed on an outside surface of the fibrous structure.

A specific treatment in which the catalyst for synthesizing theaflavins of this embodiment is contained in or fixed on the fibrous structure can be appropriately selected by those skilled in the art, and is not particularly limited. For example, the catalyst for synthesizing theaflavins may be contained in the fibrous structure by adding the catalyst for synthesizing theaflavins of this embodiment to a polymer material, kneading the mixture, and forming fibers. The catalyst for synthesizing theaflavins may be fixed on the fibrous structure such as a woven fabric and a non-woven fabric using a binder, a coupling agent, or the like. Further, the catalyst for synthesizing theaflavins is fixed on an inorganic material such as zeolite, and the inorganic material having the fixed catalyst for synthesizing theaflavins is fixed on the fibrous structure to produce a theaflavins synthesis catalyst filter. Also, a base formed of a material such as inorganic oxide particles is fixed on a fibrous base material, and immersed in a hydrate in which a material for metal nanoparticles is dissolved. Thus, the metal nanoparticles can be precipitated on a surface of the inorganic oxide particles and the like. Herein, the catalyst for synthesizing theaflavins that is contained is a concept including a case where the catalyst for synthesizing theaflavins is exposed to an outside surface of the fibrous structure.

A binder component can be appropriately selected in consideration of adhesion to the fibrous base material, and the like, and is not particularly limited. For example, a synthetic resin such as a polyester resin, an amino resin, an epoxy resin, a polyurethane resin, an acrylic resin, a water-soluble resin, a vinyl-based resin, a fluororesin, a silicone resin, a fibrin-based resin, a phenolic resin, a xylene resin, and a toluene resin, or a natural resin such as drying oil including castor oil, linseed oil, and tung oil may be used.

In a method of fixing the catalyst for synthesizing theaflavins of this embodiment on the fibrous base material, the catalyst for synthesizing theaflavins may be fixed by the above-described binder, or the like. The catalyst for synthesizing theaflavins of this embodiment is chemically bonded to a silane monomer having an unsaturated bond, or the like, by a reflux treatment, or the like, dispersed in a solvent such as methanol, applied to or immersed in a fibrous base, and irradiated with radioactive ray such as electron beam. Thus, a chemical bond may be formed by graft polymerization.

Examples of silane monomer used may include vinyltrichlorosilane, vinyltrimethoxysilane, vinyltriethoxysilane, vinyltriacetoxysilane, N-β-(N-vinylbenzylaminoethyl)-γ-aminopropyltrimethoxysilane, hydrochloride of N-(vinylbenzyl)-2-aminoethyl-3-aminopropyltrimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane 3-isocyanatepropyltriethoxysilane, bis(triethoxysilylpropyl)tetrasulfide, 3-aminopropyltrimethoxysilane, 3-aminopropyltriethoxysilane, 3-triethoxysilyl-N-(1,3-dimethyl-butylidene) propylamine, N-phenyl-3-aminopropyltrimethoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-mercaptopropylmethyldimethoxysilane, 3-mercaptopropyltrimethoxysilane, N-phenyl-3-aminopropyltrimethoxysilane, specialized aminosilane, 3-ureidopropyltriethoxysilane, 3-chloropropyltrimethoxysilane, tetramethoxysilane, tetraethoxysilane, methyltrimethoxysilane, methyltriethoxysilane, dimethyldiethoxysilane, phenyltriethoxysilane, hexamethyldisilazane, hexyltrimethoxysilane, decyltrimethoxysilane, hydrolysable group-containing siloxane, floroalkyl group-containing oligomer, methylhydrogensiloxane, and a silicone quaternary ammonium salt.

In a specific example of a method for producing the fibrous structure, for example, the catalyst for synthesizing theaflavins of this embodiment is mixed during production of a non-woven fabric produced by entangling fibers, or a mixed paper produced by mixing pulp and a binding agent, or the like, as the base. In this manner, the catalyst for synthesizing theaflavins can be disposed in a space inside of the base. Alternatively, the catalyst for synthesizing theaflavins of this embodiment may be fixed by discharging a thermoplastic resin, a reactive hot melt adhesive, or a resin to be cured through a reaction by particle rays such as ultraviolet light and an electron beam, into a fibrous shape from a nozzle; while a surface of the fibers formed by discharging has tackiness, bringing the catalyst for synthesizing theaflavins of this embodiment into contact with the fibers; and then performing a reaction curing treatment. In the fixing, the hot melt adhesive may be anchored by returning the temperature to room temperature, the reactive hot melt adhesive may be cured through a reaction due to moisture in the air, or a resin to be crosslinked by ultraviolet light or an electron beam may be cured through a reaction by irradiation with ultraviolet light or an electron beam.

Examples of the resin thus used may include a hot melt adhesive containing, as a main component, a resin such as a low density polyethylene, a liner chain low density polyethylene, polypropylene, an ethylene-vinyl acetate copolymer resin, an ethylene-methyl methacrylate copolymer resin, and an ethylene-ethyl acrylate copolymer resin, a reactive hot melt adhesive mainly containing an urethane prepolymer, and a resin to be cross linked by ultraviolet light or an electron beam, containing, as a main component, polyurethane acrylate or a polyester acrylate resin.

Next, synthesis of theaflavins using the catalyst for synthesizing theaflavins of this embodiment will be described in detail. In this embodiment, for example, there is an aspect in which the catalyst for synthesizing theaflavins according to this embodiment is brought into contact with catechins aqueous solution that is an aqueous solution in which pyrogallol-type catechin and catechol-type catechin are dissolved, to synthesize theaflavins. Herein, theaflavin represents theaflavin (TE) represented by the formula (I), theaflavin-3-O-gallate represented by the formula (II), theaflavin-3'-O-gallate represented by the formula (III), and theaflavin-3,3'-O-digallate represented by the formula (IV).

[Chemical formula 1]

(I)

[Chemical formula 2]

(II)

[Chemical formula 3]

(III)

[Chemical formula 4]

(IV)

Hereinafter, the synthesis of theaflavins according to this embodiment will be described in more detail.

In the synthesis of theaflavins according to this embodiment, catechins are used as a raw material. Catechins are classified into pyrogallol-type catechin and catechol-type catechin, and a mixture thereof is used as a raw material in this embodiment. The catechins used as a raw material may be a commercially available product or an extract from tea leaves. The pyrogallol-type catechin is represented by the following general formula (V), and the catechol-type catechin is represented by the following general formula (VI).

[Chemical formula 5]

(V)

EGC: $R^1$ = H
EGCg: $R^1$ = galloyl group

[Chemical formula 6]

(VI)

EC: $R^2$ = H
ECg: $R^2$ = galloyl group

In the formula (V), $R^3$ represents a hydrogen atom or a galloyl group. Epigallocatechin (EGC) is a compound in which $R^1$ in the formula (V) is a hydrogen atom. Epigallocatechingallate (EGCg) is a compound in which $R^1$ in the formula (V) is a galloyl group. In the formula (VI), $R^2$ represents a hydrogen atom or a galloyl group. Epicatechin (EC) is a compound in which $R^2$ in the formula (VI) is a hydrogen atom. Epicatechin gallate (ECg) is a compound in which $R^2$ in the formula (VI) is a galloyl group.

For example, catechol-type catechin such as epicatechin and pyrogallol-type catechin such as epigallocatechin as raw materials are first added to pure water, stirred overnight at a pH of 5 to 8, and dissolved, to obtain an aqueous solution (hereinafter referred to as catechins aqueous solution). The concentration of catechins in the catechins aqueous solution are not particularly limited, and can be appropriately set by those skilled in the art. It is preferable that the ratio of the concentration of metal nanoparticles supported on the catalyst for synthesizing theaflavins (μmol/mL) to the whole concentration of catechins (μmol/ml) be 1:10 or more and 1:100 or less. It is preferable that the concentration of the catechol-type catechin in the catechin aqueous solution be smaller than that of the pyrogallol-type catechin. It is desirable that the ratio of the concentration of the catechol-type catechin to that of the pyrogallol-type catechin be 1:1 to 1:10 or less. In order to easily dissolve the catechol-type catechin and the pyrogallol-type catechin, an alcohol may be mixed in the catechins aqueous solution. The pH of the catechins aqueous solution may be made acidic.

To the obtained catechins aqueous solution containing the catechol-type catechin and the pyrogallol-type catechin, the catalyst for synthesizing theaflavins of this embodiment is added to promote a reaction. For example, the reaction may be performed with stirring until, the pyrogallol-type catechin is consumed. The temperature during the reaction is not particularly limited as long as it is a temperature at which the aqueous solution is not frozen. The temperature may be 4° C. to 100° C., and is preferably a temperature equal to or higher than room temperature (15° C. to 25° C.) to lower than 100° C., at which the reaction efficiency of the catalyst is good. After completion of the reaction, a suspension containing the obtained theaflavins and the catalyst for synthesizing theaflavins are subjected to centrifugation or filtration through a filter, to remove the catalyst for synthesizing theaflavins. Thus, an aqueous solution containing the theaflavins (hereinafter referred to as theaflavins aqueous solution) is obtained. The resulting theaflavins aqueous solution may be used as it is. In addition, the theaflavins may be collected by removing water from the theaflavins aqueous solution, if necessary.

In another embodiment in which the catechins aqueous solution is brought into contact with the catalyst for synthesizing theaflavins of this embodiment, the catalyst for synthesizing theaflavins having the filter shape of this embodiment, or a filter in which the catalyst for synthesizing theaflavins of this embodiment is contained or fixed may also be used. When a powdered catalyst for synthesizing theaflavins is used, theaflavins as a product and the catalyst for synthesizing theaflavins need to be separated, for example by centrifugation after the complication of the reaction. However, when the filter is used, the separation process can be omitted. The powdered catalyst for synthesizing theaflavins of this embodiment may be placed in a cylinder with a hole or a box, or may be placed in a bag formed of a woven fabric or a knit fabric, and the bag may be immersed in the catechins aqueous solution.

In the above-described reaction process, oxygen may be added by bubbling to a reaction liquid in which the catalyst for synthesizing theaflavins according to this embodiment is added to the catechins aqueous solution. When the dissolved oxygen concentration in the reaction liquid is increased, an oxidation reaction of the catalyst for synthesizing theaflavins proceeds. An increase in yield of theaflavins can be expected.

In this embodiment, the catalyst can be easily removed from a product after production of theaflavins, compared with a case where a reaction is performed using an enzyme or the like. When the reaction is performed using an enzyme or the like, theaflavins cannot be efficiently synthesized without a specialized condition of temperature, pH, and the like. However, in this embodiment, the reaction can be efficiently performed under a wider reaction condition.

The present invention will be then described more specifically with reference to Examples. However, the present invention is not limited only to these Examples.

EXAMPLE

Preparation of Catalyst for Synthesizing Theaflavins

Example 1

0.5 mmol of $HAuCl_4 \cdot 4H_2O$ was dissolved in 100 ml of water (5 mmol/L), the resultant mixture was heated to 70° C., and the pH was adjusted with an NaOH aqueous solution to 4.8. To the aqueous solution, 5 g of zirconia powder was added as a base, and the mixture was stirred for 1 hour. After that, the mixture was separated into a solid and a liquid, and the solid was dried under reduced pressure. The obtained solid was dried under a nitrogen atmosphere at 200° C. for 4 hours, and pulverized, to obtain a gold nanoparticle-supporting catalyst for synthesizing theaflavins.

Figure 1:
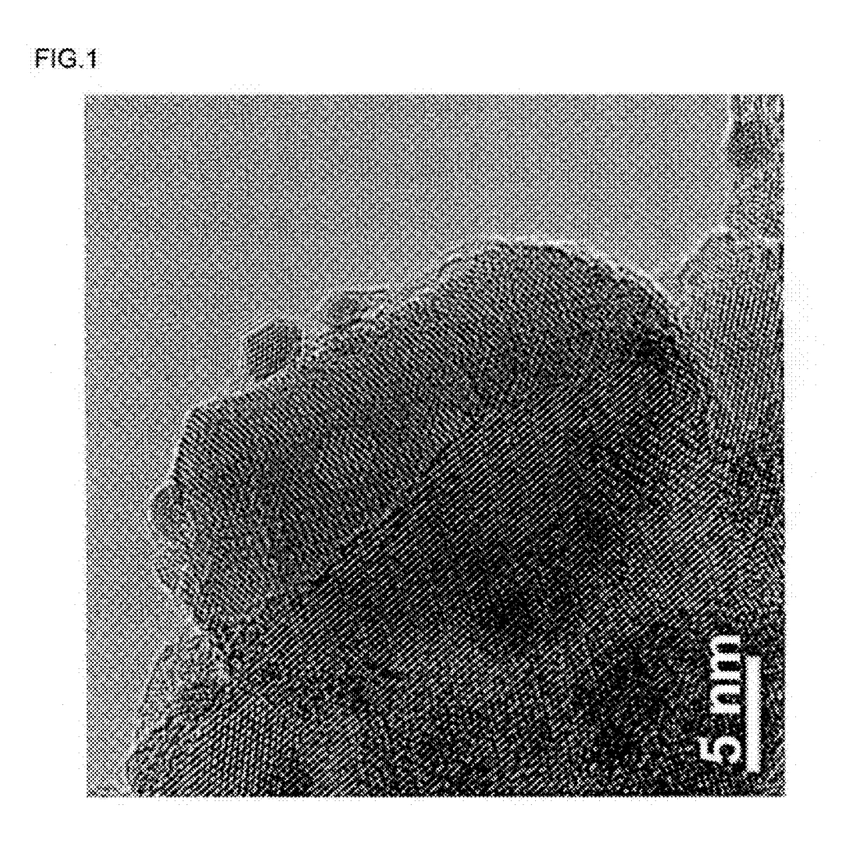
FIG. 1 is a TEM image of a catalyst for synthesizing theaflavins of Example.

The resulting catalyst for synthesizing theaflavins was observed by a transmission electron microscopy (TEM), and junction of the gold nanoparticles to zirconia particles and formation of junction interface peripheral part were confirmed. A TEM image of the catalyst for synthesizing theaflavins is shown in FIG. 1. From the TEM image, the particle diameters or 300 gold nanoparticles were measured, and averaged. The average particle diameter of the gold nanoparticles was 3.3 nm (σ=1.8 nm).

Example 2

A catalyst for synthesizing theaflavins was obtained in the same manner as in Example 1 except that the base was changed into silica powder. The average particle diameter of gold nanoparticles jointed to the base was 6.6 nm (σ=2.7 nm).

Example 3

A catalyst for synthesizing theaflavins was obtained in the same manner as in Example 1 except that the base was changed into iron (III) oxide powder. The average particle diameter of gold nanoparticles jointed to the base was 1.8 nm (σ=0.2 nm).

Example 4

A catalyst for synthesizing theaflavins was obtained in the same manner as in Example 1 except that the base was changed into titanium dioxide powder. The average particle diameter of gold nanoparticles jointed to the base was 4.1 nm (σ=2.2 nm).

Example 5

A catalyst for synthesizing theaflavins was obtained in the same manner as in Example 1 except that the base was changed into alumina powder. The average particle diameter of gold nanoparticles jointed to the base was 3.5 nm (σ=2.4 nm).

Example 6

A catalyst for synthesizing theaflavins was obtained in the same manner as in Example 1 except that the base was changed into zirconia cloth of 1 cm×0.5 cm (ZYW-30A; available from Tomoe Engineering Co., Ltd.). The average particle diameter of gold nanoparticles jointed to the base was 4.7 nm (σ=1.6 nm).

Example 7

A JIS class 1 titanium plate (with a size of 10 cm×10 cm and a thickness of 0.5 mm) was washed with ethanol. Then, the titanium plate was immersed in a sodium carbonate aqueous solution of 2 mol/L, and a direct current voltage was applied to the titanium plate for 10 minutes while spark discharge was generated on a surface of the titanium plate using a carbon electrode as a cathode and the titanium plate as an anode. As a result, a thin film of titanium oxide of rutile-type and anatase-type was formed on the surface of the titanium plate. After that, the titanium plate was washed with ion-exchanged water, and immersed in an aqueous solution of 70° C. obtained by dissolving 0.5 mmol of $HAuCl_4.4H_2O$ used in Example 1 and adjusting the pH to 4.8 for 1 hour, to obtain a catalyst for synthesizing theaflavins. The average particle diameter of gold nanoparticles jointed to the surface of the thin film of titanium oxide was 4.6 nm (σ=2.0 nm).

Example 8

An aluminum plate of JIS H1070 (with a size of 10 cm×10 cm and a thickness of 0.5 mm) was immersed in a 5% aqueous solution of sodium hydroxide heated to 50° C. for 1 minute, resulting in delipidization. The aluminum plate was immersed in a 3% aqueous solution of nitric acid, and immersed in an aqueous solution containing 2 mol sodium carbonate and 0.2 mol sodium fluoride. A direct current voltage was applied to the aluminum plate for 5 minutes while spark discharge was generated on a surface of the aluminum plate using a carbon electrode as a counter electrode. As a result, a thin film of γ-alumina was formed on the surface of the aluminum plate. After that, gold nanoparticles were precipitated on a surface of the thin film of γ-alumina under the same condition as in Example 7 to obtain a catalyst for synthesizing theaflavins. The average particle diameter of the gold nanoparticles jointed to the surface of the oxidized thin film was 3.2 nm (σ=1.9 nm).

Example 9

1 mmol of ammonium tetrachloropalladate $(NH_4)2PdCl_4$ was dissolved in 200 mL of water, the aqueous solution was heated to 70° C., and the pH was adjusted with an NaOH aqueous solution to 11. To the above-described $(NH_4)2PdCl_4$ aqueous solution, 5 g of commercially available zirconium oxide powder (PCS, available from Nippon Denko Co., Ltd.) was added, the mixture was stirred for 1 hour, and water was then removed, to obtain powder. The powder was washed with pure water. After the washing, the powder was collected by centrifugation (3,000 rpm, 10 minutes), dried under reduced pressure for 12 hours, heated at 200° C. under an air atmosphere for 4 hours to obtain a catalyst for synthesizing theaflavins. The average particle diameter of palladium nanoparticles precipitated on a surface of zirconium oxide was 8.6 nm (σ=2.2 nm).

Example 10

γ-alumina (TAIMICRON, available from Taimei Chemicals Co., Ltd.) was dispersed in water by a homogenizer to prepare a γ-alumina suspension. Subsequently, the γ-alumina suspension was mixed in a methanol solution in which 0.5% by mass of aminopropylethoxysilane was added, and the mixture was treated at 50° C. for 2 hours, to introduce aminopropylethoxysilane into a surface of γ-alumina. The γ-alumina was then filtered, and dried at 120° C. for 1 hour, to bond aminopropylethoxysilane to the surface of γ-alumina. Subsequently, γ-alumina in which aminopropylethoxysilane was introduced was dispersed in an aqueous solution containing 0.066 mmol/L of stannous chloride and 0.095 mmol/L of hydrochloric acid by a homogenizer. 0.5 mmol of $(NH_4)2PdCl_4$ solution that was dissolved in 100 mL of water was mixed to the solution to coordinate and adsorb palladium ions on the surface of γ-alumina. The γ-alumina in which palladium ions were coordinated and adsorbed was collected by filtration, and then dried at 200° C. for 2 hours to obtain a catalyst for synthesizing theaflavins in which nanoparticles of palladium oxide (PdO) were anchored. The average particle diameter of palladium oxide nanoparticles precipitated on the surface of γ-alumina was 10.4 nm (σ=3.8 nm).

Example 11

Platinum bis(acetylacetonate) and α-alumina were mixed in a mortar so that the amount of platinum was 5% by weight relative to 1 g of α-alumina. The resulting mixture was fired at 450° C. for 4 hours, and further fired at 450° C. for 2 hours under a hydrogen atmosphere, to obtain a catalyst for synthesizing theaflavins in which platinum nanoparticles were anchored. The average particle diameter of platinum nanoparticles precipitated on a surface of α-alumina was 14.8 nm (σ=2.0 nm).

Comparative Example 1

In Comparative Example 1, zirconia powder used in Example 1 was used.

Comparative Example 2

In Comparative Example 2, silica powder used in Example 2 was used.

Comparative Example 3

In Comparative Example 3, iron (III) oxide powder used in Example 3 was used.

Comparative Example 4

In Comparative Example 4, titanium dioxide powder used in Example 4 was used.

Comparative Example 5

In Comparative Example 5, alumina powder used in Example 5 was used.

Synthesis of Theaflavin

Theaflavin was synthesized using each sample of Examples 1 to 11 and Comparative Examples 1 to 5.

Epicatechin and epigallocatechin as raw materials were first added in each amount of 4 µmol/L to pure water, and stirred overnight to dissolve, thereby obtaining a catechins aqueous solution. 1 mL of each catechins aqueous solution was placed in a 5-mL tube. Each sample (0.5 mL) of Examples and Comparative Examples was added to the catechins aqueous solution at room temperature to obtain each reaction liquid. The reaction liquid was subjected to a reaction with stirring for 4 hours. In Examples 1 to 8, each dispersion liquid in which the Au concentration was adjusted to 0.8 µmol/mL was added as the above-described sample to the catechins aqueous solution. In Examples 9 and 10, each dispersion liquid in which the Pd concentration was adjusted to 0.8 µmol/mL was added as the above-described sample to the catechins aqueous solution. In Example 11, a dispersion liquid in which the Pt concentration was adjusted to 0.8 µmol/mL was added as the above-described sample to the catechins aqueous solution. In Comparative Examples, a dispersion liquid in which each base was dispersed in the same amount as that of the catalyst for synthesizing theaflavins used in each Example was added to the catechins aqueous solution as the above-described sample. After completion of the reaction, the reaction liquid was subjected to filtration through a filter with a pore diameter of 0.45 µm to remove the catalyst.

Measurement Condition of Catechins

A product obtained by the above-described method was analyzed by high performance liquid chromatography (HPLC) under the following conditions, and the amount of produced theaflavins was calculated. A gradient condition in the analysis is shown in Table 1.

Column: ZORBAX SB-C18 (manufactured by Agilent Technologies)
4.6×50 nm, φ20 µm
Injection volume: 20 µL
Flow rate: 1.0 mL/min
A: 0.1% phosphoric acid
B: acetonitrile
Column temperature: 40° C.
Detection: 280 nm

TABLE 1

| TIME | GRADIENT (%) | |
|---|---|---|
| (min) | A | B |
| 0 | 95 | 5 |
| 4.5 | 89 | 11 |
| 7.5 | 75 | 25 |
| 12.5 | 75 | 25 |
| 47.5 | 5 | 95 |
| 52.5 | 5 | 95 |
| 52.6 | 95 | 5 |
| 60.0 | 95 | 5 |

Figure 2:
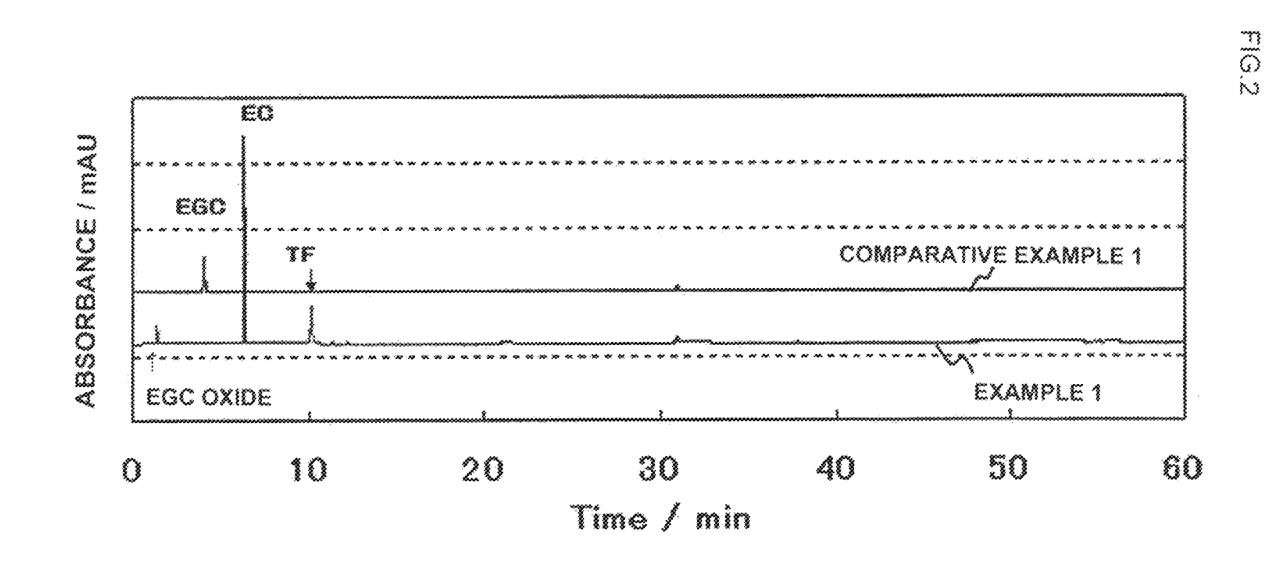
FIG. 2 is a result of analysis of a theaflavin aqueous solution obtained in Example.

The results are shown in Table 2. Chromatograms according to Example 1 and Comparative Example 1 are shown in FIG. 2. As understood from FIG. 2, a peak corresponding to theaflavin represented by TF was confirmed in the chromatogram of the sample according to Example 1. Even in the samples according to other Examples, the similar chromatogram as in Example 1 was obtained.

TABLE 2

| | KIND OF METAL | AVERAGE OF METAL NANO-PARTICLES (nm) | STANDARD DEVIATION (nm) | SYNTHESIS AMOUNT OF THEAFLAVIN (µmol/mL) |
|---|---|---|---|---|
| EXAMPLE 1 | Au | 3.3 | 1.8 | 0.030 |
| EXAMPLE 2 | Au | 6.6 | 2.7 | 0.045 |
| EXAMPLE 3 | Au | 1.8 | 0.2 | 0.082 |
| EXAMPLE 4 | Au | 4.1 | 2.2 | 0.104 |
| EXAMPLE 5 | Au | 3.5 | 2.4 | 0.002 |
| EXAMPLE 6 | Au | 4.7 | 1.6 | 0.022 |
| EXAMPLE 7 | Au | 4.6 | 2.0 | 0.054 |
| EXAMPLE 8 | Au | 3.2 | 1.9 | 0.004 |
| EXAMPLE 9 | Pd | 8.6 | 2.2 | 0.038 |
| EXAMPLE 10 | Pd | 10.4 | 3.8 | 0.054 |
| EXAMPLE 11 | Pt | 14.8 | 2.0 | 0.095 |
| COMPARATIVE EXAMPLE 1 | — | — | — | 0 |
| COMPARATIVE EXAMPLE 2 | — | — | — | 0 |
| COMPARATIVE EXAMPLE 3 | — | — | — | 0 |
| COMPARATIVE EXAMPLE 4 | — | — | — | 0 |
| COMPARATIVE EXAMPLE 5 | — | — | — | 0 |

As shown in Table 2, in all Examples, synthesis of theaflavin was confirmed.

Confirmation of Theaflavin

In order to confirm in detail whether or not theaflavin was produced in the aforementioned reaction, analysis using LC-MS was performed. As an analysis sample, a sample in which the catalyst for synthesizing theaflavins of Example 1 was used as a catalyst was used. A peak that was estimated to correspond to theaflavin was extracted using liquid chromatogram (LC), and measured by mass spectrum (MS). The results are shown in FIG. 3.

Figure 3:
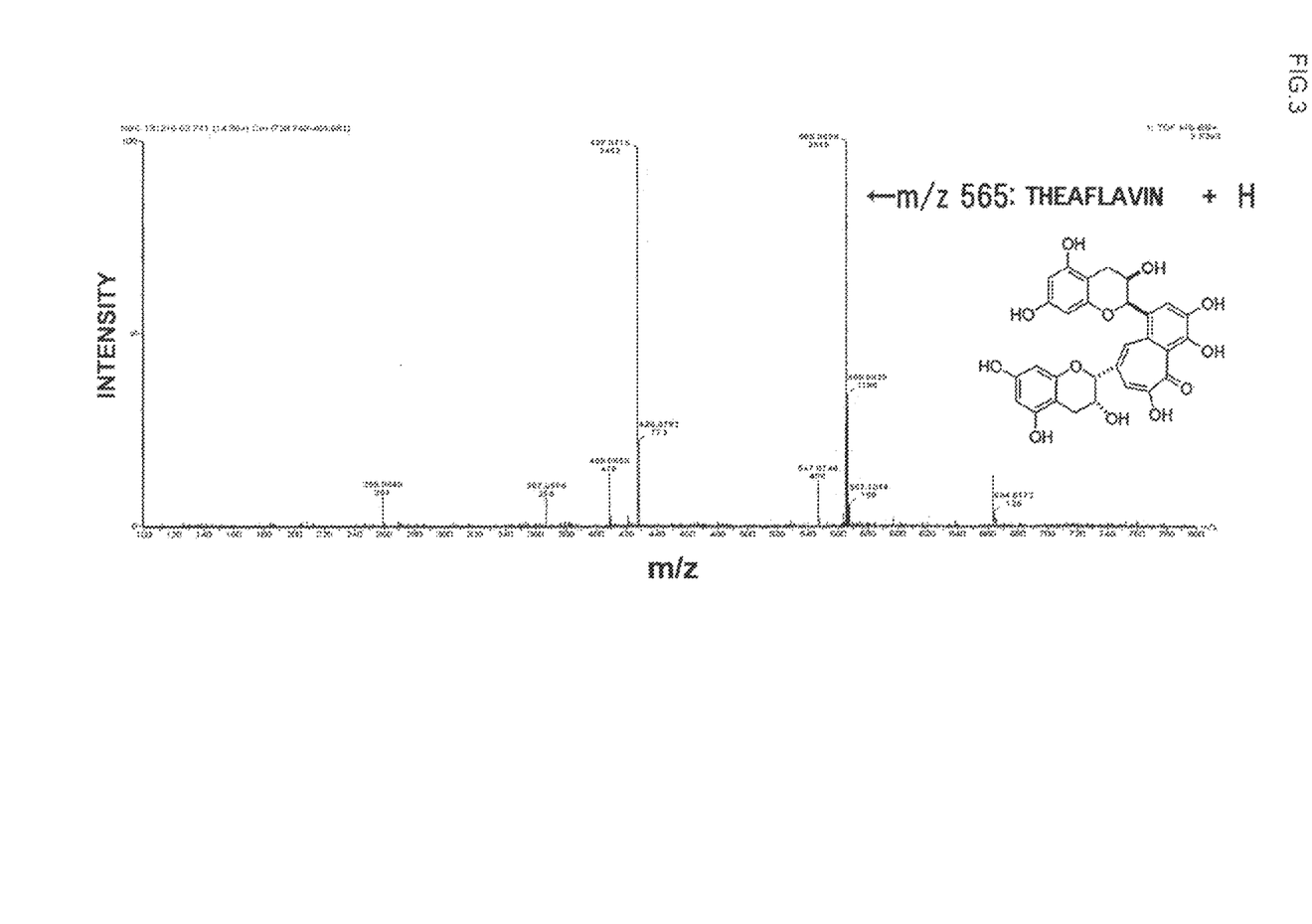
FIG. 3 is a result of analysis of a theaflavin aqueous solution obtained in Example.

From the results of FIG. 3, the molecular weight in which hydrogen ions (H) were added to the molecular weight of theaflavin was confirmed. Therefore, synthesis of theaflavin was confirmed.

From the results of FIG. 3, a substance synthesized by a reaction of pyrogallol-type catechin and catechol-type catechin was not a substance other than theaflavin. Therefore, in theaflavin synthesized by a synthesis method using the catalyst for synthesizing theaflavins of this embodiment, peaks other than that of theaflavin were very few, and it was confirmed that synthesis of theaflavins was achieved while production of by-product was suppressed.

The invention claimed is:

1. A method for synthesizing theaflavins, comprising:
bringing a catalyst for synthesizing theaflavins comprising:
a base having an anchored part comprising an inorganic material on a surface, and metal nanoparticles that are anchored to the anchored part and have a particle diameter of 0.5 nm or more and 100 nm or less,
into contact with a catechins aqueous solution comprising dissolved pyrogallol-type catechin and catechol-type catechin,
to synthesize the theaflavins.

2. The method according to claim 1, wherein the metal nanoparticles are at least one selected from the group consisting of Au, Pd, Pt, and oxides thereof.

3. The method according to claim 1, wherein the anchored part further comprises a metal oxide.

4. The method according to claim 3, wherein the metal oxide is at least one selected from the group consisting of $SiO_2$, $ZrO_2$, $Fe_2O_3$, and $TiO_2$.

* * * * *